(12) United States Patent
Zanone et al.

(10) Patent No.: US 7,090,832 B2
(45) Date of Patent: Aug. 15, 2006

(54) COOLING AGENTS, PHARMACEUTICAL COMPOSITIONS HAVING COOLING AGENTS AND PROCESSES FOR MAKING AND USING SAME

(75) Inventors: John Zanone, Montville Township, NJ (US); Roger E. Stier, Clifton, NJ (US)

(73) Assignee: Firmenich SA, Geneva (CH)

( * ) Notice: Subject to any disclaimer, the term of this patent is extended or adjusted under 35 U.S.C. 154(b) by 302 days.

(21) Appl. No.: 10/272,710

(22) Filed: Oct. 17, 2002

(65) Prior Publication Data

US 2003/0049327 A1    Mar. 13, 2003

Related U.S. Application Data

(62) Division of application No. 09/716,034, filed on Nov. 17, 2000, now Pat. No. 6,497,859.

(51) Int. Cl.
*A61K 7/16* (2006.01)
*A61K 47/00* (2006.01)

(52) U.S. Cl. .................. 424/49; 424/434; 424/440; 426/3

(58) Field of Classification Search ................. 424/434, 424/49, 440; 426/3
See application file for complete search history.

(56) References Cited

U.S. PATENT DOCUMENTS

| 4,060,091 | A |   | 11/1977 | Watson et al. |
|-----------|---|---|---------|---------------|
| 4,136,163 | A | * | 1/1979  | Watson et al. ............... 424/54 |
| 5,009,893 | A |   | 4/1991  | Cherukuri et al. |
| 5,244,670 | A | * | 9/1993  | Upson et al. ............... 424/439 |
| 5,372,824 | A | * | 12/1994 | Record et al. .................. 426/3 |
| 5,434,292 | A | * | 7/1995  | Saita et al. .................... 560/51 |
| 5,698,181 | A |   | 12/1997 | Luo |
| 5,885,594 | A | * | 3/1999  | Nilsen et al. ............... 424/401 |
| 6,106,865 | A | * | 8/2000  | Staniforth et al. .......... 424/489 |
| 6,627,233 | B1| * | 9/2003  | Wolf et al. .................... 426/3 |

* cited by examiner

*Primary Examiner*—Vickie Kim
(74) *Attorney, Agent, or Firm*—Norris, McLaughlin & Marcus

(57) ABSTRACT

The invention pertains to cooling agents comprising N-substituted p-menthane-3-carboxamides, menthyl acetate and solubilizer, and methods for making the cooling agents. The invention also concerns pharmaceutical compositions comprising the cooling agents, including tablets, suspensions and liquid solutions having active pharmaceutical agents for treating upper gastrointestinal tract distress, and methods for treating upper gastrointestinal tract distress in humans.

10 Claims, 1 Drawing Sheet

COOLING AGENTS, PHARMACEUTICAL COMPOSITIONS HAVING COOLING AGENTS AND PROCESSES FOR MAKING AND USING SAME

CROSS-REFERENCE TO RELATED APPLICATIONS

This is a divisional application of Ser. No. 09/716,034, filed Nov. 17, 2000, now U.S. Pat. No. 6,497,859.

BACKGROUND OF THE INVENTION

1. Field of the Invention

The invention relates to cooling agent compositions that impart a cooling sensation to the skin and mucous membranes of the body, particularly the mouth, nose, throat and gastrointestinal tract during consumption and methods for making cooling agents. The cooling agents comprise N-substituted p-menthane-3-carboxamides, menthyl acetate and a solubilizer, in spray dried form. The invention also concerns pharmaceutical compositions comprising the cooling agents, including tablets, suspensions and liquid solutions having active ingredients for treating upper gastrointestinal tract distress, and methods for treating upper gastrointestinal tract distress in humans. The cooling agents may also be used in a sundry of edible products such as confectionary products, including chewing gum, hard and soft candies and the like.

2. The Prior Art

Cooling agents and compositions are used in a sundry of consumer goods. U.S. Pat. No. 4,136,163 describes the use of N-substituted p-menthane-3-carboxamides in edible and potable compositions, toiletries, medicaments, and miscellaneous compositions such as envelopes, postage stamps and adhesive compositions. The N-substituted p-menthane-3-carboxamides are described as having a physiological cooling effect on the skin and on the mucous membranes of the body, particularly the mouth, nose, throat and gastrointestinal tract. U.S. Pat. No. 4,060,091 describes the use of N-substituted p-menthane-3-carboxamides in tobacco or tabacco containing products.

In pharmaceutical compositions, such as antacids, useful for treating upper gastrointestinal tract distress, such as heartburn, indigestion, stomachache and the like, cooling agents are generally employed as excipients to provide cooling sensation when the pharmaceutic composition is consumed. Generally, the active pharmaceutical agent in pharmaceutical compositions for treating upper gastrointestinal tract distress will not immediately begin to relieve the condition causing the distress. Cooling agents, used in the pharmaceutical compositions as excipients, however, provide cooling sensation to the mouth, throat and gastrointestinal tract so that the pharmaceutical composition will be perceived by the consumer as acting faster to alleviate the gastrointestinal distress. Thus, the consumer is provided with the sensation of relief although the active principle of the pharmaceutical composition has not begun to alleviate the conditions causing the distress.

U.S. Pat. No. 5,244,670 describes ingestible pharmaceutical compositions for treating upper gastrointestinal tract distress comprising active principle and 3,1-methoxy propane 1,2-diol ("MPD"). U.S. Pat. No. 5,009,893 describes chewing gum compositions comprising a cooling agent having from about 5% to about 70%, by weight, of menthol and from about 30% to about 95%, by weight, of N-substituted p-menthane-3-carboxamide compounds. The combination of the menthol and the carboxamide compounds in the amounts specified in U.S. Pat. No. 5,009,893 are said to be necessary for cooling and breath freshening properties. U.S. Pat. No. 5,698,181 describes breath-freshening edible compositions comprising a cooling composition of essential ingredients of about 94% to about 99.999%, by weight, menthol and about 0.001% to about 6%, by weight, N-substituted p-menthane-3-carboxamides.

There is a consumer demand, and consequently a need, for cooling agents that provide faster cooling sensation when consumed and longer lasting effect. The art of cooling agents for pharmaceutical compositions, confectionary products and like comestibles is constantly evolving.

It was an object of the invention to develop new cooling agents for use in comestible goods, like pharmaceutical compositions, and confectionary products, like gum, that provide cooling effect and long lasting freshness.

We have discovered that cooling agents comprising the combination of N-substituted p-menthane-3-carboxamides, menthyl acetate and solubilizer, in spray dried form, act synergistically to provide cooling sensation and a long lasting freshness effect. The cooling agents are particularly useful in pharmaceutical compositions for treating upper gastrointestinal tract distress.

In the present Specification, all parts and percentages are by weight/weight unless otherwise specified. The term "by weight of cooling agent components" as used herein means the weight percentage based on the total weight of all of the components of the cooling agent, such as the carboxamide, menthyl acetate and solubilizer. The term "by weight of the combination" as used herein means the weight percentage based on the total weight of all of the components of the cooling agent and the carrier and residual water in the spray dried particles. The term "by weight of the pharmaceutical composition" as used herein means the weight percentage based on the total weight of all components of the pharmaceutical composition.

SUMMARY OF THE INVENTION

The invention pertains to cooling agents comprising N-substituted p-menthane-3-carboxamides, menthyl acetate and a solubilizer. The finished cooling agent is in spray dried form and, in that state, can be used in a number of products, including pharmaceutical compositions, particularly those for treating upper gastrointestinal tract distress, and confectionary products. The menthyl acetate is combined with the N-substituted p-menthane-3-carboxamides and the combination acts synergistically to provide the cooling effect and long lasting freshness that characterizes the invention.

The N-substituted p-menthane-3-carboxamides, menthyl acetate and solubilizer can be made through spray drying processes. For example, the cooling agent can be combined with a carrier and water to form an emulsion for spray drying to obtain spray dried particulate material comprising the cooling agent and a carrier. The solubilizer in the cooling agent prevents the N-substituted p-menthane-3-carboxamides from crystallizing out of solution during the spray drying process, which requires heat to maintain solubility.

DETAILED DESCRIPTION OF THE INVENTION

Figure 1:
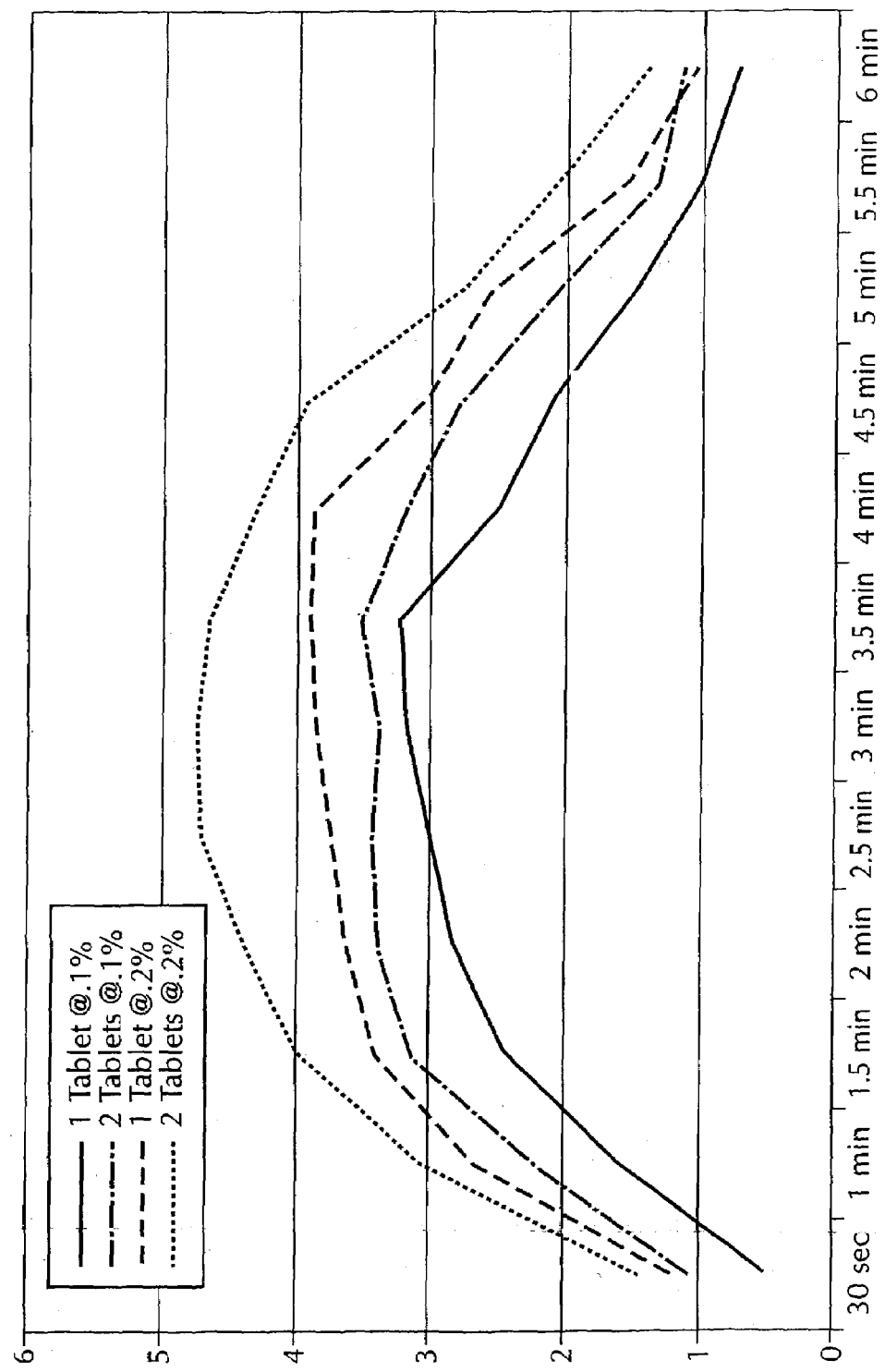
FIG. 1 is a graph showing average sensory perception for cooling at time intervals after ingestion of pharmaceutical compositions comprising the cooling agents.

The cooling agents comprise about 1% to about 20%, preferably about 10% to about 20%, N-substituted p-menthane-3-carboxamides, by weight of cooling agent components, about 1% to about 10%, preferably about 3% to about 6%, menthyl acetate, by weight of cooling agent components, and about 60% to about 85%, preferably about 75% to about 85%, solubilizer, by weight of cooling agent components. The cooling agents may also consist essentially of the foregoing components or may consist of the foregoing components. It was unexpectedly discovered that the combination of these compounds within these compositional ranges, particularly the N-substituted p-menthane-3-carboxamides and menthyl acetate, act synergistically to provide cooling sensation and long lasting freshness. The solubilizer stabilizes the solution so that the N-substituted p-menthane-3-carboxamides will not crystallize out during the spray drying process as a result of the heat that must be applied during the process.

The N-substituted p-menthane-3-carboxamides used in the invention generally have the following formula:

[Structure: p-menthane ring with CONR'R'' substituent and isopropyl group]

where

1) R', when taken separately, is hydrogen or an aliphatic radical containing up to 25 carbon atoms;

2) R'', when taken separately is hydroxy, or an aliphatic radical containing up to 25 carbon atoms, with the proviso that when R' is hydrogen R'' may also be an aryl radical of up to 10 carbon atoms and selected from the group consisting of substituted phenyl, phenalkyl or substituted phenalkyl, naphthyl and substituted naphthyl, pyridyl; and 3) R' and R'', when taken together with the nitrogen atom to which they are attached, represent a cyclic or heterocyclic group of up to 25 carbon atoms, e.g. piperidino, morpholino and the like.

In the above definitions "aliphatic" is intended to include any straight-chained, branched-chained or cyclic free radical or aromatic unsaturation, and thus embraces alkyl, cycloalkyl, alkenyl, cycloalkenyl, alkynyl, hydroxyalkyl, acyloxyalkyl, alkoxy, alkoxyalkyl, aminoalkyl, acylaminoalkyl, carboxyalkyl and similar combinations.

Typical values for R' and R'' when aliphatic are methyl, ethyl, propyl, butyl, isobutyl, n-decyl, cyclopropyl, cyclohexyl, cyclopentyl, cycloheptylmethyl, 2-hydroxyethyl, 3-hydroxy-n-propyl, 6-hydroxy-n-hexyl, 2-aminoethyl, 2-acetoxyethyl, 2-ethylcarboxyethyl, 4-hydroxybut-2-ynyl, carboxymethyl and the like.

When R'' is aryl typical values are benzyl, naphthyl, 4-methoxyphenyl, 4-hydroxyphenyl, 4-methylphenyl, 3-hydroxy-4-methylphenyl, 4-fluorophenyl, 4-nitrophenyl, 2-hydroxynaphthyl, pyridyl, and the like.

The preferred species is N-ethyl p-menthane-3-carboxamide, which is commercially known as "WS-3". N-ethyl p-menthane-3-carboxamide is available from Millennium Specialty Chemicals, Jacksonville, Fla., USA.

The N-substituted p-menthane-3-carboxamides may be readily prepared by conventional methods, such as by the reaction of the corresponding acid chloride (obtained by reacting p-menthane-3-carboxylic acid with thionyl chloride) with the appropriate mono- or di-substituted amine. The reaction will usually be carried out in solution in the presence of a hydrogen chloride receptor, e.g. sodium hydroxide. The reaction proceeds smoothly at room temperature.

The carboxamide compounds exhibit both geometric and optical isomerism and, depending on the starting materials and the methods used in their preparation, the compounds may be isometrically pure, i.e. consisting of one geometric or optical isomer, or they may be isomeric mixtures, both in the geometric and optical sense. The basic p-menthane structure is a chair-shaped molecule which can exist in cis or trans forms. Substitution of the carboxyl or amide group into the 3-position gives rise to four configurational or geometric isomers depending upon whether the substitution is axially or equatorially into the cis or trans isomer, the four isomers being related as menthol is to neomenthol, isomenthol, and neoisomenthol. In general it is found that in the compounds used in this invention the equatorially substituted derivatives have the greater cooling effect than the axial compounds and are to be preferred. Substitution of the amide group in the 3-position of the p-menthane structure also gives rise to optical isomerism, each of the above-mentioned four geometric isomers, existing in d, l and dl forms.

When either R' and R'' is aliphatic, the preferred values are $C_1$–$C_9$ straight or branched chain alkyl, $C_1$–$C_9$ straight or branched chain hydroxyalkyl or aminoalkyl and $C_1$–$C_4$ acrylated derivatives thereof, and —$C_nH_{2n}COR'''$ or —$C_nH_{2n}COOR'''$, where —$C_nH_{2n}$ is a straight or branched chain alkylene radical in which n is an integer of from 1–6 and R''' is hydrogen or a $C_1$–$C_8$ alkyl or hydroxyalkyl group, preferably a $C_1$–$C_4$ straight chain alkyl group.

In general the monosubstituted compounds, i.e. where R' is H, are preferred although di-substituted compounds where R' and R'' are both $C_1$–$C_3$ alkyl may be used. Most preferred of all are compounds where R' is H and R'' is $C_1$–$C_3$ alkyl, $C_1$–$C_4$ hydroxyalkyl, or —$CH_2COOR'''$, where R''' is $C_1$–$C_4$ alkyl.

Also included are compounds where R' is H and R'' is hydroxy or substituted phenyl, e.g. alkylphenyl, hydroxyphenyl, alkoxyphenyl, halophenyl of up to 10 carbon atoms, phenalkyl or substituted phenalkyl, e.g. benzyl, naphthyl or substituted naphthyl, and compounds where R' and R'' are joined to form a cyclic group. When so joined R' and R'' preferably represent an alkylene chain, optionally interrupted by oxygen, which together with the nitrogen atom to which R' and R'' are attached forms a 5- or 6-membered heterocyclic ring.

Menthyl acetate is a colorless liquid having a chemical formula of $C_{12}H_{22}O_2$. Menthyl acetate is a constituent of peppermint oil and can be derived from the natural oil, or obtained by chemical synthesis through processes that would be known to one skilled in the art. Menthyl acetate is available from Haarmann & Reimer, South Plainfield, N.J., USA.

The solubilizer provides stability to the N-substituted p-menthane-3-carboxamide during the spray drying process by preventing the carboxamide from crystallizing out as a result of the heat that is applied during the spray drying process. Suitable solubilizers are miglyol which are mixed esters of capric and acrylic acids that are esterified on glycerin, ethoxylated hydrogenated castor oil, polysorbates, glycerin, triglycerides and fatty acids such as lauric acid, myristic acid, palmitic acid, stearic acid, oleic acid, linolenic acid and the like. The preferred solubilizer is miglyol, such as that available from LIPO Chemicals, Inc., Paterson, N.J., USA under the tradename LIPONATE™ (GC-K).

The cooling agent can be incorporated into a spray dried particulate material through a spray drying process. The N-substituted p-menthane-3-carboxamide, menthyl acetate and solubilizer are generally combined with a suitable carrier, such as Salseal 200 available from National Starch, Bridgewater, N.J., USA or starches as would be known to one skilled in the art, and water to form an emulsion. The emulsion is spray dried in either a conical or flat bottom spray drier, depending on production volume, at speed rates, temperature, pressure and nozzle size to obtain spray dried particulate material comprising the cooling agent having a particle size permitting 100% of the particles to pass through a 40 mesh screen. The ratio of cooling agent, e.g. N-substituted p-menthane-3-carboxamide, menthyl acetate and solubilizer, to carrier in the particulates is about 50:50 to about 90:10, preferably about 70:30, by weight of the combination.

The cooling agents and the particulates comprising the cooling agent may be incorporated in a number of consumer products, including pharmaceutical compositions and confectionary products. When used in pharmaceutical compositions, particularly those for treating upper gastrointestinal tract distress, such as heartburn, indigestion, stomachache and the like, the cooling agents, or the particulate comprising the cooling agents, are excipients which may be combined with active pharmaceutical agents and other excipients and then be compressed into tablets or used in liquid form, such as solutions, suspensions or emulsions and the like.

Active pharmaceutical agents for treating upper gastrointestinal tract distress are those materials which are safe and effective when administered orally for treating disorders of the upper gastrointestinal tract (typically the stomach and/or esophagus) which result in symptoms of upper gastrointestinal tract distress. Such active pharmaceutical agents include antacid agents and acid secretion prevention agents (e.g., $H_2$ receptor-blocking antisecretory agents). Antacid agents include, for example, aluminum carbonate, aluminum hydroxide, aluminum phosphate, aluminum hydroxy-carbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumina silicates, magnesium carbonate, magnesium glycinate, magnesium hydroxide, magnesium oxide, magnesium trisilicate, sucralfate, and mixtures thereof. Examples of acid secretion prevention agents include cimetidine, ranitidine, famotidine, omeprazole, and mixtures thereof. Other useful pharmaceutical actives include bismuth-containing agents such as, for example, bismuth subsalicylate, bismuth aluminate, bismuth citrate, bismuth subcitrate, bismuth nitrate, bismuth subcarbonate, bismuth subgalate, and mixtures thereof. A particularly preferred bismuth salt is bismuth subsalicylate.

Preferred antacid agents are aluminum hydroxide, magnesium hydroxide, dihydroxy aluminum sodium carbonate, calcium carbonate, and mixtures thereof. Most preferred is calcium carbonate.

The pharmaceutical compositions comprise a safe and effective amount of at least one active pharmaceutical agent, useful for treating upper gastrointestinal tract distress. Typically the active pharmaceutical agent(s) are from about 1% to about 99%, preferably from about 30% to about 40%, by weight of the pharmaceutical composition.

The pharmaceutical compositions also comprise the cooling agents described herein which comprise N-substituted p-menthane-3-carboxamide, menthyl acetate and solubilizer. The cooling agent and, optionally residual water and/or carrier when the cooling agent is used in the particulate form, are generally present in the pharmaceutical compositions in an amount of about 0.01% to about 1%, preferably about 0.05% to about 0.25%, by weight of the pharmaceutical composition.

In addition, excipients other than the cooling agent may optionally be included in the pharmaceutical compositions. The term "excipient(s)", as used herein, means, in addition to the cooling agent, one or more compatible solid or liquid filler diluents or encapsulating substances which are suitable for oral administration to a human and encompasses all of the ingredients of the pharmaceutical compositions except the active pharmaceutical agent. The term "compatible", as used herein, means that the components of the compositions of the invention are capable of being commingled with the active pharmaceutical agent, and with each other, in a manner such that there is no interaction which would substantially reduce the pharmaceutical efficacy of the compositions under ordinary use situations. Excipients must, of course, be of sufficiently high purity and sufficiently low toxicity to render them suitable for administration to the human being.

Some examples of substances which can serve as excipients are sugars such as lactose, glucose and sucrose; starches such as cornstarch and potato starch; cellulose and its derivatives such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobroma; polyols such as propylene glycol, glycerine, sorbitol, mannitol, and polyethylene glycol; agar; and alginic acid; as well as other nontoxic compatible substances used in pharmaceutical formulations. Wetting agents and lubricants such as sodium lauryl sulfate, as well as coloring agents, flavoring agents, sweetening agents (including normutritive sweeteners such as aspartame and saccharine), tableting agents, stabilizers, antioxidants, and preservatives, can also be present. Other compatible pharmaceutical additives and actives which are not active pharmaceutical agents useful for treating upper gastrointestinal tract distress (e.g., NSAI drugs; pain killers; muscle relaxants) may be included in the compositions of the present invention. Also, it is to be noted that in addition to the cooling agents described herein, other materials having cooling properties may optionally be included within the excipients, such as menthol cooling compounds and mixtures thereof. Menthol or other materials having cooling properties, however, are not necessary to the unexpected and surprising cooling performance (i.e. the cooling sensation and long lasting freshness perceived by the consumer) of the cooling agents comprising N-substituted p-menthane-3-carboxamides, menthyl acetate and solubilizer.

The choice of excipients to be used in conjunction with the active pharmaceutical agent is basically determined by the dose form for the pharmaceutical compositions. The preferred dosage forms are tablets, especially chewable tablets, capsules and the like, comprising a safe and effective amount of the active pharmaceutical agent(s). Dosage forms may also include liquid solutions, liquid suspensions and the like. Excipients suitable for the preparation of dosage forms for oral administration are well-known in the art. Their selection will depend on secondary considerations like taste, cost, shelf stability, and can be made without difficulty by a person skilled in the art.

The excipients employed in the ingestible compositions are used at concentrations sufficient to provide a practical size to dosage relationship. Typically, excipients comprise from about 1% to about 99%, preferably from about 85% to about 99%, by weight of the pharmaceutical composition.

The pharmaceutical compositions comprising the cooling agent or the particulate described herein, comprising N-substituted p-menthane-3-carboxamide compounds, menthyl acetate and solubilizer, preferably miglyol, can be employed in methods for treating upper gastrointestinal tract distress in humans. The method comprises orally administering to a human a safe and effective amount of at least one active pharmaceutical agent useful for treating upper gastrointestinal tract distress and an amount of the cooling agent effective to provide a cooling sensation to the mouth, throat and for the gastrointestinal tract. The preferred mode of administration for this method is through an ingestible composition, most preferably through an ingestible tablet.

EXAMPLE

Cooling agent comprising 15% N-ethyl p-menthane-3-carboxamide, 5% menthyl acetate and 80% miglyol 810 from LIPO Chemicals, Inc., all by weight of cooling agent components, with a carrier in particulate form was incorporated into tablet form pharmaceutical compositions comprising calcium carbonate, an active pharmaceutical agent of an antacid agent, and orange fruit flavorings. Tablets containing cooling agent with carrier, the particulate, at 0.1% by weight of the pharmaceutical composition and at 0.2% by weight of the pharmaceutical composition were prepared.

The tablets were then provided to a tasting panel for sensory Total Oral Perception using a sliding ballot scale of 0 for no cooling effect to 6 for high cooling effect. Each panelist sampled one and two tablets of each pharmaceutical composition comprising cooling agent in particulate form with carrier at 0.1% and 0.2% by weight of the pharmaceutical composition.

The testing study was performed for 3 days with two tasting sessions daily. The testing protocol for one tablet required each panelist to place one tablet in the mouth, chew twenty times and swallow. Cooling perception measurements were recorded privately by each panelist at 30 seconds after swallowing the sample tablet and thereafter at 30 second intervals for a total time of six minutes. The testing protocol for two tablets required the panelist to place one fruit tablet in the mouth, chew twenty times, swallow, place the second tablet in the mouth, chew 20 times and swallow. Cooling perception measurements were recorded privately by each panelist at 30 seconds after swallowing the second tablet contents and thereafter at 30 second intervals for a total time of six minutes.

The ballots were reviewed to obtain average perception scores based on a sliding scale of 0–6 for the three day trials for one tablet and two tablets having the cooling agent with carrier, in particulate form at, respectively, 0.1% and 0.2% by weight of the pharmaceutical composition. The results are presented in FIG. 1.

What is claimed is:

1. A pharmaceutical composition comprising from about 1% to about 99% by weight of the pharmaceutical composition of at least one active pharmaceutical agent selected from the group consisting of antacid agents, acid secretion prevention agents, bismuth containing agents and mixtures thereof and from about 1% to about 99% by weight of the pharmaceutical composition excipients comprising at least one cooling agent in spray dried form, wherein the cooling agent comprises a) N-substituted p-menthane-3-carboxamide of the formula:

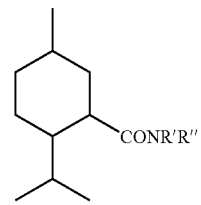

where
R', when taken separately, is hydrogen or an aliphatic radical containing up to 25 carbon atoms; and
R", when taken separately is hydroxy, or an aliphatic radical containing up to 25 carbon atoms, with the proviso that when R' is hydrogen R" may also be an aryl radical of up to 10 carbon atoms and selected from the group consisting of substituted phenyl, phenalkyl, substituted phenalkyl, naphthyl, substituted naphthyl, and pyridyl; and
R' and R", when taken together with the nitrogen atom to which they are attached, represent a cyclic or heterocyclic group of up to 25 carbon atoms,
b) menthyl acetate wherein the menthyl acetate and the N-substituted p-menthane-3-carboxamide act synergistically to provide a cooling effect, and
c) solubilizer of mixed esters of capric and acrylic acids esterified on glycerin wherein said solubilizer is present in an amount sufficient to prevent the N-substituted p-methane-3-carboxamines from crystallizing out of solution during the spray drying process.

2. The pharmaceutical composition of claim 1 wherein the cooling agent comprises from about 1% to about 20% of the N-substituted p-menthane-3-carboxamide compounds, about 1% to about 10% of the menthyl acetate and about 60% to about 85% of the solubilizer all by weight of cooling agent components.

3. The pharmaceutical composition of claim 1 further comprising a carrier.

4. The pharmaceutical composition of claim 1 wherein the N-substituted p-menthane-3-carboxamide is N-ethyl p-methane-3-carboxamide.

5. The pharmaceutical composition of claim 1 wherein the excipients comprise menthol.

6. The pharmaceutical composition of claim 1 wherein the antacid agents are selected from the group consisting of aluminum carbonate, aluminum hydroxide, aluminum phosphate, aluminum hydroxy-carbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumina silicates, magnesium carbonate, magnesium glycinate, magnesium hydroxide, magnesium oxide, magnesium trisilicate, sucralfate, and mixtures thereof.

7. The pharmaceutical composition of claim 1 wherein the acid secretion prevention agents are selected from the group consisting of cimetidine, ranitidine, famotidine, omeprazole, and mixtures thereof.

8. The pharmaceutical composition of claim 1 wherein the bismuth containing agents are selected from the group consisting of bismuth subsalicylate, bismuth aluminate, bismuth citrate, bismuth subcitrate, bismuth nitrate, bismuth subcarbonate, bismuth subgalate, and mixtures thereof.

9. A method for treating upper gastrointestinal tract distress in humans comprising orally administering through an ingestible composition a safe and effective amount of at least one active pharmaceutical agent selected from the group consisting of antacid agents, acid secretion prevention agents, bismuth containing agents and mixtures thereof, and a cooling agent in spray dried form comprising a) N-substituted p-menthane-3-carboxamide of the formula:

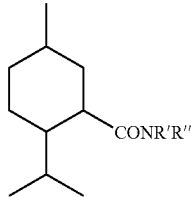

where

R', when taken separately, is hydrogen or an aliphatic radical containing up to 25 carbon atoms; and R'', when taken separately is hydroxy, or an aliphatic radical containing up to 25 carbon atoms, with the proviso that when R' is hydrogen R'' may also be an aryl radical of up to 10 carbon atoms and selected from the group consisting of substituted phenyl, phenalkyl, substituted phenalkyl, naphthyl, substituted naphthyl, and pyridyl; and R' and R'', when taken together with the nitrogen atom to which they are attached, represent a cyclic or heterocyclic group of up to 25 carbon atoms, b) menthyl acetate wherein the menthyl acetate and the N-substituted p-menthane-3-carboxamide act synergistically to provide a cooling effect, and c) solubilizer of mixed esters of capric and acrylic acids esterified on glycerin wherein said solubilizer is present in an amount sufficient to prevent the N-substituted p-methane-3-carboxamines from crystallizing out of solution during the spray drying process.

10. The method of claim 9 wherein the ingestible composition is in the form of tablet.

* * * * *